July 25, 1972 H. C. SWIM ET AL Plant Pat. 3,244
ROSE PLANT
Filed March 11, 1971
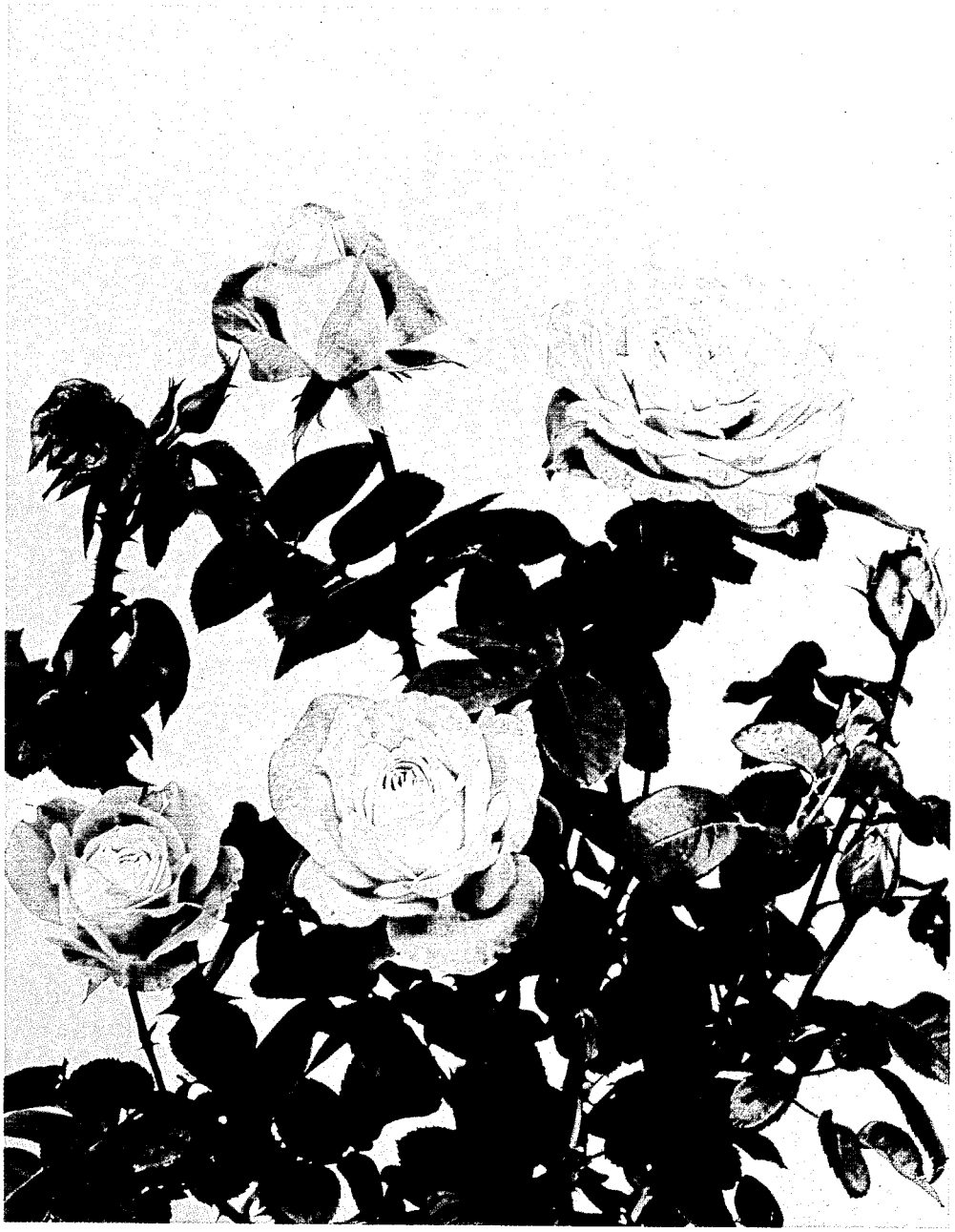
Inventors.
H. C. Swim
O. L. Weeks
By: Robbins Robb
Attorneys.

United States Patent Office

Plant Pat. 3,244
Patented July 25, 1972

3,244
ROSE PLANT

Herbert C. Swim and O. L. Weeks, Ontario, Calif., assignors to O. L. Weeks, doing business as Weeks Wholesale Rose Grower, Ontario, Calif.

Filed Mar. 11, 1971, Ser. No. 123,479
Int. Cl. A01h *5/00*
U.S. Cl. Plt.—11 1 Claim

The present invention relates to a new and distinct variety of rose plant of the hybrid tea class, which was originated by us by crossing the rose variety known as "Tiffany" (Plant Pat. No. 1,304) with an unnamed and unpatented rose variety have a rather complex breeding background involving crosses with "Fandango" (Plant Pat. No. 894), 'Roundelay" (Plant Pat. No. 1,280), "Happiness" (Plant Pat. No. 911), and Tiffany. In the final cross, the variety "Tiffany" was the seed parent and the unnamed seedling was the pollen parent.

As the result of this breeding, we have produced a new and improved rose variety which is distinguished from its parents, as well as from all other rose varieties of which we are aware, as evidenced by the following unique combination of characteristics which are outstanding in the new variety:

(1) A well-branched, symmetrical and tall plant habit;

(2) Unusually strong and long cutting stems;

(3) Better than average foliage substance and resistance to powdery mildew;

(4) A habit of bearing the flowers singly, with almost complete absence of cluster blooms;

(5) A medium to very large flower size of double and high-centered form; and (6) A distinctive, attractive and unusual flower color, with the outside surface of the petals blending from medium pink to delicate pink and then to cream color at the base, and the inside surface of the petals being strong pink at their outer edges, blending to pale pink and then to cream color at the base, and the center of the fully opened flower having a most unusual brownish-lavender shade.

In comparison with its seed parent "Tiffany," our new variety is not as tall, but has longer cutting stems for the most part; more thorns than this parent; a more double and more high-centered bloom form; the flowers have a two-toned pink color blend, while those of "Tiffany" are essentially one tone of pink color; and the new variety has no flower fragrance, while the flowers of "Tiffany" have a moderate fragrance.

As compared with its unnamed pollen parent, the new variety is a more upright and taller grower; its foliage has much more substance and is a much darker green color and lacks some of the purple in-tones that are characteristic of the foliage of this parent; the flowers of the new variety are high-centered and very double, while those of this parent are not high-centered and have fewer petals; and the flowers of the new variety are essentially a two-toned pink color as compared with the rather dark red flower color of the parent variety.

Asexual reproduction of our new variety by budding, as performed at Chino, Calif., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Md., except where general color terms of ordinary dictionary significance are obvious:

Type: Hardy; tall; bush; outdoor; seedling; for cut flowers and for garden decoration.

Class: Hybrid tea.

Breeding: Seedling.

*Seed parent.*—"Tiffany."

*Pollen parent.*—An unnamed seedling.

Propagation: Holds its distinguishing characteristics through succeeding propagations by budding.

FLOWERS

Locality where grown and observed: Chino and Ontario, Calif.

Flowers Borne: Singly to stem; on strong, long stems.

Quantity of bloom: From free to abundant, outdoors.

Continuity: From intermittent to continuous.

Fragrance: None.

Bud:

*Peduncle.*—Medium length; medium caliper; erect; entirely smooth. Color: Medium green.

*Before calyx breaks.*—Size: Medium. Form: From short to medium length; pointed; with a conspicuous neck; with slender, bristlellike foliaceous parts extending beyond the top of the bud equal to ¾ or more of its length.

*As calyx breaks.*—Color: Between Strong Red, Hue 5 R 4/12 and Moderate Red, Hue 2.5 R 4/10 at tip, but the visible body portion being essentially cream color, blended with a very pale yellow with streaks of the tip colors and sometimes blending into the same, but lighter.

*As first petal opens.*—Size: From small to medium. Form. Mostly ovid. Color: Outside—a small mixture of Brilliant Greenish Yellow, Hue 7.5 Y 9/8 and Brilliant Greenish Yellow, Hue 10 Y 9/9 at basal tip of petal, progressing into some in-tones of Deep Pink, Hue 2.5 R 6/11 on some petals and into lighter than Pale Pink, Hue 2.5 R 9/3 on others; inside—considerably brighter than Strong Purplish Red, Hue 7.5 RP 5/12, with a small portion of between Vivid Yellow, Hue 5 Y 8/2 and Brilliant Yellow, Hue 5 Y 9/9 at basal tip.

*Opening.*—Opens up well.

Bloom:

*Size (when fully open).*—From medium to very large; from 4 inches to 5 inches.

*Petalage.*—Very double, with no stamens showing; from 46 to 52 petals; arranged regularly.

*Form.*—Very full and high-centered; petals being at first tightly rolled outward, and remaining fairly tightly rolled outward at maturity.

Petals:

*Texture.*—Thin; soft.

*Appearance.*—Inside: Satiny. Outside: Satiny.

*Shape.*—Outside: From broadly round to oval, with apex flat and usually with 1 notch. Intermediate: From round to oval, with apex flat. Inside: From round to oval, and usually with 1 notch.

This description of a newly opened flower was made from a rose grown outdoors during the month of October at Ontario, Calif.

*Color.*—Outer petal: Outside surface—Light Purplish Pink, Hue 5 RP 8/5, with an occasional streaking of Strong Purplish Pink, Hue 5 RP 7/9, and with a small segment of Brilliant Yellow Green, Hue 2.5 GY 9/8 at base; inside surface—Strong Purplish Red, Hue 7.5 RP 4/11, but brighter, with a small basal segment of Brilliant Greenish Yellow, Hue 10 Y 9/9. Intermediate petal: Outside surface—considerably lighter than Light Purplish Pink, Hue 7.5 RP 8/5, with small basal segment of Brilliant Yellow, Hue 5 Y 9/9; inside surface—between Strong Purplish Pink, Hue 7.5 RP 7/10, and Strong Purplish Pink, Hue 5 RP 7/9, with small basal segment of Vivid Yellow, Hue 5 Y 8/12. Inner petal: Outside surface—considerably lighter than Light Purplish Pink, Hue 7.5 RP 8/5, with small basal area of Brilliant Yellow, Hue 2.5 Y 9/9; inside surface—a little darker than Strong Purplish Pink, Hue 7.5 RP 7/10, with a small basal area of Vivid Yellow, Hue 5 Y 8/12.

This description was made from a rose that was open for three days outdoors during the month of October at Ontario, Calif.

*Color.*—Outer petal: Outside surface—between cream color and Strong Pink, Hue 10 RP 7/8 and Deep Pink, Hue 10 RP 6/12 going into Strong Purplish Red, Hue 10 RP 5/12 on the fringe, with a small basal tip segment between Brilliant Greenish Yellow, Hue 10 Y 9/9 and Brilliant Yellow Green, Hue 2.5 GY 9/8; inside surface—small basal tip of Greenish Yellow, Hue 10 Y 9/9, blending into cream color just above base and then progressing to considerably brighter than Strong Purplish Red, Hue 10 RP 5/12. Inner petal: outside surface—much paler than Light Yellowish Pink, Hue 2.5 YR 9/3, with a small basal segment of Brilliant Greenish Yellow, Hue 7.5 Y 9/8; inside surface—Strong Pink, Hue 10 RP 7/8, with a small basal segment of Brilliant Greenish Yellow, Hue 10 Y 9/9.

*General color effect.*—Newly opened flower: A combination of Deep Pink, Hue 10 RP 6/12, Strong Purplish Red, Hue 10 RP 5/12, and brighter than Strong Purplish Red, Hue 10 RP 4/12, with the Purplish Red in-tones being revealed as the petals turn slightly outward and creating an overall 3-toned effect, with a blending into a light cream to brownish lavender at the center of the open bloom. 3-days open: High center gives an impression of pale pink to brownish lavender, progressing to a stronger purplish pink toward the outer petals and going further to a deep purplish pink, with the turned outward fringes of the outer petals appearing as strong purplish red.

*Behavior.*—Drop off cleanly.

*Flower longevity.*—On bush in garden: 5 days or more in blooming seasons. Cut roses grown outdoors and kept at living room temperature: From 4 to 6 days in October.

REPRODUCTIVE ORGANS

Stamens: Many; arranged irregularly about pistils; tucked in calyx.

Filaments: Medium length; most with anthers.

*Color.*—From white to yellow.

Anthers: Open at various times.

*Color.*—From white to yellow.

Pollen: Moderately abundant.

*Color.*—Gold yellow.

Pistils: Medium number.

Styles: Very uneven; medium length; medium caliper; bunched.

Stigma:

*Color.*—Yellow.

Ovaries: All protruding from calyx.

Hips: None observed.

Sepals: Permanent; moderately long; spear-shaped; recurved.

*Color.*—Outside: Medium green. Inside: Grayish green.

Seeds: None observed.

PLANT

Foliage:

*Leaves.*—Compound of 3, 5 and 7 leaflets; very normal; moderately large; moderately heavy; semi-glossy.

*Leaflets.*—Shape: Ovate. Apex: Obtuse. Base: Truncate. Margin: Simply serrate.

*Color.*—Mature: Upper surface—moderately light to dark green; under surface—moderately light green. Young: upper surface—from bronze to red; under surface—moderately red.

*Rachis (the supporting stem of the compound leaf).*—Medium weight. Upper side: Grooved. Under side: Moderately prickly.

*Stipules.*—Moderately short; moderately narrow; medium wide; with short to medium length points turning out at an angle of less than 45°.

*Disease resistance.*—Good resistance to mildew and other rose diseases, as determined by comparison with other rose varieties grown under comparable conditions at Chino and Ontario, Calif.

Growth:

*Habit.*—Upright; much branched.

*Growth.*—Free and vigorous.

*Canes.*—Moderately heavy.

*Main stems.*—Color: Dull green. Large prickles: Many; medium length; almost straight; with fairly short, narrow base; color—brown. Small prickles: Many; color—brown. Hairs: None.

*Branches.*—Color: Dull green. Large prickles: Many; from medium length to long; straight; with short, narrow base; color—brown at base to dull green. Small prickles: Many; color—from green to brown. Hairs: Few; color—from brown to reddish.

*New shoots.*—Color: From dull green to brown. Large prickles: Several; from short to medium length; straight; with short, narrow base; color—some dull green and some brownish. Small prickles: Few; color—from brown to reddish. Hairs: Few; color—from brown to reddish.

We claim:

1. A new and distinct variety of Rose Plant of the hybrid tea class, substantially as herein shown and described, characterized particularly as to novelty by the unique combination of a well-branched, symmetrical and tall plant habit, unusually strong and long cutting stems, better than average foliage substance and resistance to powdery mildew, a habit of bearing the flowers singly, with almost complete absence of cluster blooms, a medium to very large flower size of double and high-centered form, and a distinctive, attractive and unusual flower color, with the outside surface of the petals blending from medium pink to delicate pink and then to cream color at the base, and the inside surface of the petals being strong pink at their outer edges, blending to pale pink and then to cream color at the base, and the center of the fully opened flower having a most unusual brownish-lavender shade.

No references cited.

ROBERT E. BAGWILL, Primary Examiner